(12) United States Patent
Fantini et al.

(10) Patent No.: US 10,087,226 B2
(45) Date of Patent: Oct. 2, 2018

(54) CHIMERIC PEPTIDE THAT INTERACTS WITH CELL MEMBRANE GANGLIOSIDES

(71) Applicant: Universite D'Aix-Marseille, Marseilles (FR)

(72) Inventors: Jacques Fantini, Septemes-les-vallons (FR); Nouara Yahi, Septemes-les-vallons (FR)

(73) Assignee: Universite D'Aix-Marseille, Marseilles (FR)

( * ) Notice: Subject to any disclaimer, the term of this patent is extended or adjusted under 35 U.S.C. 154(b) by 0 days.

(21) Appl. No.: 15/125,237

(22) PCT Filed: Mar. 10, 2015

(86) PCT No.: PCT/EP2015/054968
§ 371 (c)(1),
(2) Date: Sep. 12, 2016

(87) PCT Pub. No.: WO2015/135942
PCT Pub. Date: Sep. 17, 2015

(65) Prior Publication Data
US 2017/0073383 A1    Mar. 16, 2017

(30) Foreign Application Priority Data
Mar. 11, 2014    (EP) .................................... 14305353

(51) Int. Cl.
*C07K 14/47*    (2006.01)
*A61K 38/00*    (2006.01)

(52) U.S. Cl.
CPC .......... *C07K 14/4711* (2013.01); *C07K 14/47* (2013.01); *A61K 38/00* (2013.01)

(58) Field of Classification Search
None
See application file for complete search history.

(56) References Cited

FOREIGN PATENT DOCUMENTS

| WO | WO-03/015812 | 2/2003 |
|---|---|---|
| WO | WO-2014/031697 | 2/2014 |

OTHER PUBLICATIONS

UniProtKB—L0K8S3 (L0K8S3_HALHC), downloaded from www.uniprot.org/uniprot/L0K8S3.txt?version=1 and published online on Mar. 6, 2013.*

Fantini, et al., "Molecular Basis for Glycosphingolipid-Binding Specificity of [alpha]-Synuclein: Key Role of Tyrosine 39 in Membrane Insertion", Journal of Molecular Biology, vol. 408, No. 4, May 1, 2011, pp. 654-669.

Stockl, et al., "[alpha]-Synuclein Oligomers: an Amyloid Pore?", Molecular Neurobiology, vol. 47, No. 2, Sep. 6, 2012, pp. 613-621.

Yahi, et al., "Deciphering the Glycolipid Code of Alzheimer's and Parkinson's Amyloid Proteins Allowed the Creation of a Universal Ganglioside-Binding Peptide", Plos One, vol. 9, No. 8, Aug. 20, 2014, p. e104751.

* cited by examiner

*Primary Examiner* — Christina Bradley
(74) *Attorney, Agent, or Firm* — Cesari and McKenna, LLP

(57) ABSTRACT

The invention relates to a chimeric peptide displaying the ganglioside-binding properties of both α-synuclein and β-amyloid peptide. Such peptide is useful in preventing or treating any condition which involves gangliosides as cell surface receptor sites, including neurodegenerative disorders, infectious diseases, or tumors.

Figure 1A:
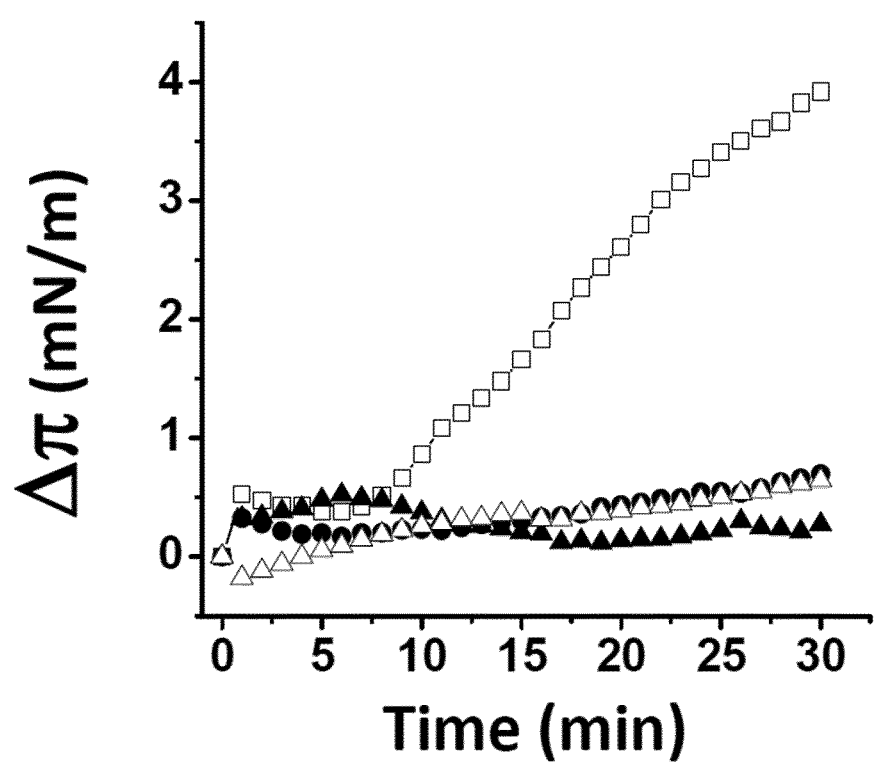

8 Claims, 11 Drawing Sheets
Specification includes a Sequence Listing.

SEQUENCE LISTING

```
<160> NUMBER OF SEQ ID NOS: 11

<210> SEQ ID NO 1
<211> LENGTH: 10
<212> TYPE: PRT
<213> ORGANISM: artificial sequence
<220> FEATURE:
<223> OTHER INFORMATION: chimeric peptide

<400> SEQUENCE: 1

Glu Gly Val Leu Tyr Val Gly His His Thr
1               5                   10

<210> SEQ ID NO 2
<211> LENGTH: 12
<212> TYPE: PRT
<213> ORGANISM: artificial sequence
<220> FEATURE:
<223> OTHER INFORMATION: chimeric peptide
<220> FEATURE:
<221> NAME/KEY: MISC_FEATURE
<222> LOCATION: (1)..(1)
<223> OTHER INFORMATION: Xaa at position 1 (X1) can be a lysine, an
      arginine or a histidine
<220> FEATURE:
<221> NAME/KEY: MISC_FEATURE
<222> LOCATION: (12)..(12)
```

```
<223> OTHER INFORMATION: Xaa at position 12 (X2) can be a lysine, an
      arginine or a histidine

<400> SEQUENCE: 2

Xaa Glu Gly Val Leu Tyr Val Gly His His Thr Xaa
1               5                   10

<210> SEQ ID NO 3
<211> LENGTH: 12
<212> TYPE: PRT
<213> ORGANISM: artificial sequence
<220> FEATURE:
<223> OTHER INFORMATION: chimeric peptide

<400> SEQUENCE: 3

Lys Glu Gly Val Leu Tyr Val Gly His His Thr Lys
1               5                   10

<210> SEQ ID NO 4
<211> LENGTH: 12
<212> TYPE: PRT
<213> ORGANISM: Homo sapiens

<400> SEQUENCE: 4

Lys Glu Gly Val Leu Tyr Val Gly Ser Lys Thr Lys
1               5                   10

<210> SEQ ID NO 5
<211> LENGTH: 12
<212> TYPE: PRT
<213> ORGANISM: Homo sapiens

<400> SEQUENCE: 5

Arg His Asp Ser Gly Tyr Glu Val His His Gln Lys
1               5                   10

<210> SEQ ID NO 6
<211> LENGTH: 12
<212> TYPE: PRT
<213> ORGANISM: artificial sequence
<220> FEATURE:
<223> OTHER INFORMATION: chimeric peptide

<400> SEQUENCE: 6

Arg Glu Gly Val Leu Tyr Val Gly His His Thr Arg
1               5                   10

<210> SEQ ID NO 7
<211> LENGTH: 12
<212> TYPE: PRT
<213> ORGANISM: artificial sequence
<220> FEATURE:
<223> OTHER INFORMATION: chimeric peptide

<400> SEQUENCE: 7

Arg Glu Gly Val Leu Tyr Val Gly His His Thr Lys
1               5                   10

<210> SEQ ID NO 8
<211> LENGTH: 12
<212> TYPE: PRT
<213> ORGANISM: artificial sequence
<220> FEATURE:
<223> OTHER INFORMATION: chimeric peptide

<400> SEQUENCE: 8
```

```
Lys Glu Gly Val Leu Tyr Val Gly His His Thr Arg
1               5                   10

<210> SEQ ID NO 9
<211> LENGTH: 10
<212> TYPE: PRT
<213> ORGANISM: artificial sequence
<220> FEATURE:
<223> OTHER INFORMATION: chimeric peptide
<220> FEATURE:
<221> NAME/KEY: MISC_FEATURE
<222> LOCATION: (2)..(2)
<223> OTHER INFORMATION: Xaa at position 2 (X1) is any amino acid
<220> FEATURE:
<221> NAME/KEY: MISC_FEATURE
<222> LOCATION: (3)..(3)
<223> OTHER INFORMATION: Xaa at position 3 (X2) is any amino acid
<220> FEATURE:
<221> NAME/KEY: MISC_FEATURE
<222> LOCATION: (4)..(4)
<223> OTHER INFORMATION: Xaa at position 4 (X3)  is any amino acid
<220> FEATURE:
<221> NAME/KEY: MISC_FEATURE
<222> LOCATION: (10)..(10)
<223> OTHER INFORMATION: Xaa at position 10 (X4) is a threonine or
      glutamine

<400> SEQUENCE: 9

Glu Xaa Xaa Xaa Tyr Val Gly His His Xaa
1               5                   10

<210> SEQ ID NO 10
<211> LENGTH: 12
<212> TYPE: PRT
<213> ORGANISM: Artificial Sequence
<220> FEATURE:
<223> OTHER INFORMATION: Reversed chimeric peptide
<220> FEATURE:
<221> NAME/KEY: MISC_FEATURE
<222> LOCATION: (1)..(1)
<223> OTHER INFORMATION: Xaa at position 1 is K, R, or H
<220> FEATURE:
<221> NAME/KEY: MISC_FEATURE
<222> LOCATION: (12)..(12)
<223> OTHER INFORMATION: Xaa at position 12 is K, R, or H

<400> SEQUENCE: 10

Xaa Glu His His Gly Val Leu Tyr Val Gly Thr Xaa
1               5                   10

<210> SEQ ID NO 11
<211> LENGTH: 12
<212> TYPE: PRT
<213> ORGANISM: Artificial Sequence
<220> FEATURE:
<223> OTHER INFORMATION: reversed chimeric peptide

<400> SEQUENCE: 11

Lys Glu His His Gly Val Leu Tyr Val Gly Thr Lys
1               5                   10
```

CHIMERIC PEPTIDE THAT INTERACTS WITH CELL MEMBRANE GANGLIOSIDES

CROSS REFERENCE TO RELATED APPLICATIONS

This application is the National Stage of International Application No. PCT/EP2015/054968, filed on Mar. 10, 2015, which claims the benefit of European Application No. 14305353.6, filed on Mar. 11, 2014. The contents of both applications are hereby incorporated by reference in their entirety.

The present invention relates to a chimeric peptide which interacts with cell surface glycolipids and has therapeutic applications in neurodegenerative disorders, infectious diseases, and cancers.

BACKGROUND OF THE INVENTION

Plasma membrane glycolipids serve as primary attachment sites for a broad range of infectious and amyloid proteins (Fantini, 2003). For instance, both GM1 and GM3 gangliosides have been involved in the pathophysiology of Alzheimer's and Parkinson's diseases (Oikawa et al, 2009; Wu et al, 2012).

In a recent study of the glycolipid binding specificity of α-synuclein, the protein associated with Parkinson's disease, Fantini et al identified the 34-45 fragment of the protein as the shortest active glycolipid binding domain (Fantini and Yahi, 2011a). This short linear motif of 12 amino acid residues confers to the protein a high specificity of interaction for GM3, a ganglioside preferentially expressed by astrocytes. This motif shares structural homology with the 5-16 fragment of Alzheimer's β-amyloid peptide (Aβ). Yet the glycolipid-binding domain of Aβ does not recognize GM3, but GM1, a ganglioside abundantly expressed at the level of post-synaptic membranes.

SUMMARY OF THE INVENTION

The inventors have now deciphered the biochemical code controlling the glycolipid-binding specificity of Aβ and α-synuclein and have created a chimeric peptide displaying the ganglioside-binding properties of both proteins.

The present invention thus provides a peptide comprising
a) amino acid sequence E-X1X2X3-YVGHH-X4 (SEQ ID NO: 9),
  wherein at least one of X1, X2, or X3, being a glycine or a serine residue, while the other(s) of X1, X2, or X3 are any amino acid; and
  X4 is a threonine or glutamine;
b) a sequence deriving from SEQ ID NO: 9 by one or more chemical modifications that protect the peptide against proteolysis, or
c) a substantially homologous sequence deriving from SEQ ID NO: 9 by one or more conservative substitutions,
  it being understood that the peptide comprises two consecutive histidine residues.

The peptide has 10 to 30 amino acids.

In a preferred embodiment, the present invention provides a peptide, which preferably comprises from 12 to 20 amino acids, comprising
a) amino acid sequence EGVLYVGHHT (SEQ ID NO: 1), or
b) a sequence deriving from SEQ ID NO: 1 by one or more chemical modifications that protect the peptide against proteolysis, or
c) a substantially homologous sequence deriving from SEQ ID NO: 1 by one or more conservative substitutions,
  it being understood that the peptide comprises two consecutive histidine residues.

A preferred peptide consists of KEGVLYVGHHTK (SEQ ID NO: 3).

Such peptide is useful in preventing or treating any condition which involves gangliosides as cell surface receptor sites, including neurodegenerative disorders, infectious diseases, or tumors.

Another subject of the invention is a nucleic acid that encodes the chimeric peptide as defined herein. A further subject of the invention is a vector comprising said nucleic acid, which is preferably an adenovirus or a lentivirus vector.

LEGENDS TO THE FIGURES

Figure 1B:
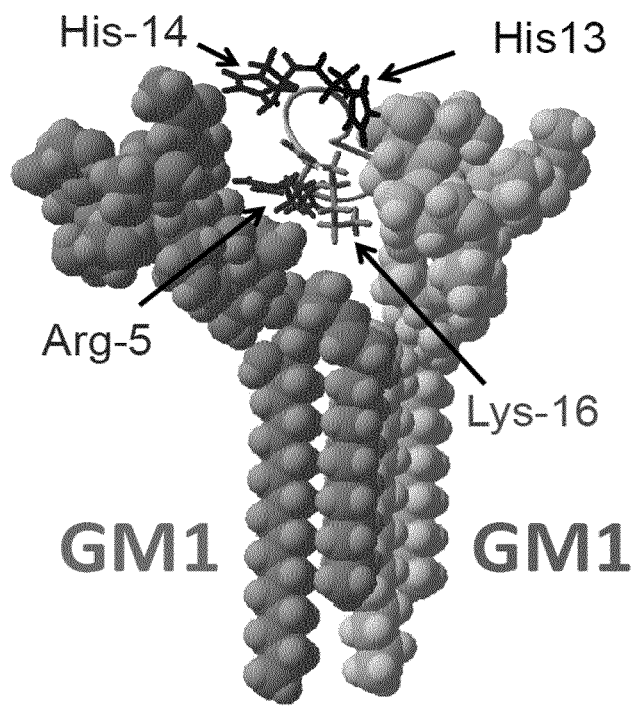

FIGS. 1A and 1B show that Both His-13 and His-14 residues are involved in the binding of Aβ5-16 to GM1.

A. A monolayer of ganglioside GM1 was prepared at an initial surface pressure of 17.5 mN·m$^{-1}$. After equilibration, the wild-type Aβ5-16 (open squares), or mutant Aβ5-16/H13A (full triangles), Aβ5-16/H14A (full circles), Aβ5-16/H13A/H14A (open triangles) peptides were injected in the aqueous subphase underneath the monolayer. The data show the evolution of the surface pressure following the injection of peptides (10 µM) in the aqueous subphase underneath the monolayer. Each experiment was performed in triplicate and one representative curve is shown (S.D.<10%). B. Molecular model of Aβ5-16 interacting with two GM1 molecules arranged into a chalice-like receptacle.

Figure 1C:
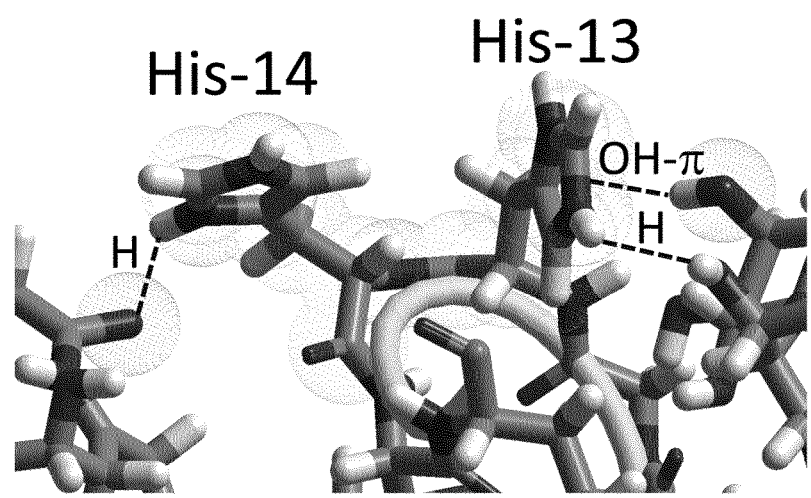

FIG. 1C shows molecular interactions between the chimeric α-syn34-45/HH peptide and a chalice-shaped dimer of GM1.

Figure 2:
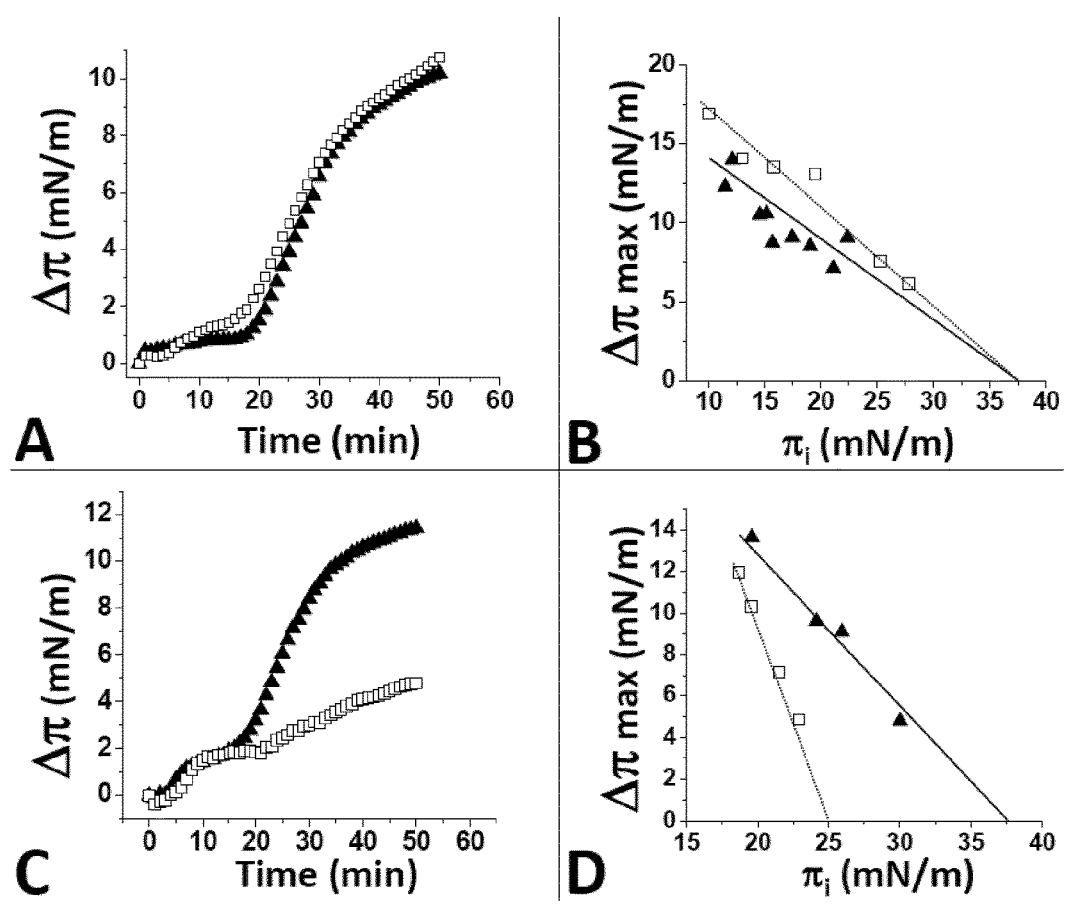

FIG. 2: The introduction of His residues within the SBD of α-syn does not alter GM3 recognition and increase its affinity for GM1.

Left panels. Kinetics of interaction of wild-type α-syn34-45 (full triangles) and double mutant α-syn34-45/HH (open squares) with a monolayer of GM3 (A) or GM1 (C). In each case the monolayer was prepared at an initial surface pressure of 17.5 mN·m$^{-1}$. All experiments were performed in triplicate and one representative curve is shown (S.D.<15%).

Right panels. Interaction of wild-type α-syn34-45 (full triangles) and double mutant α-syn34-45/HH (open squares) with GM3 (B) or GM1 monolayers (D) prepared at various values of the initial surface pressure. The maximal surface pressure increase (Δπmax) was determined after reaching the equilibrium. The critical pressure of insertion is indicated by the intercept of the slopes with the x-axis.

Figure 3A:
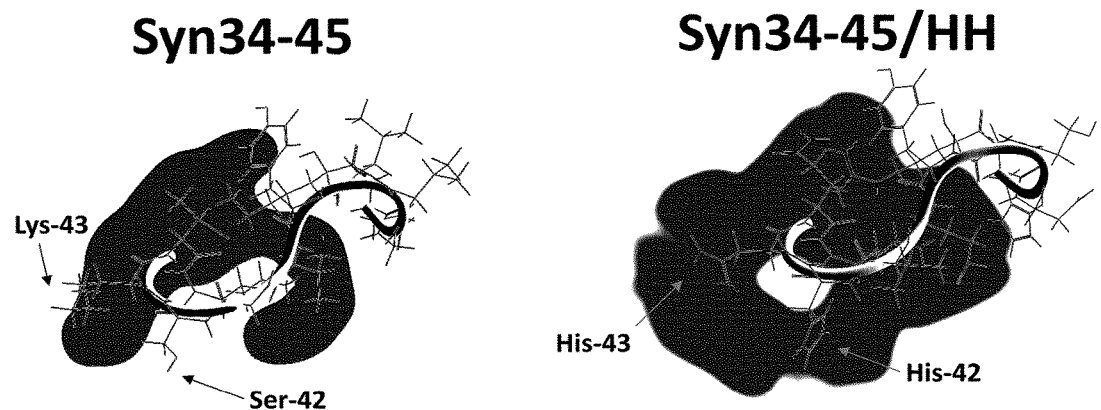
Figure 3B:
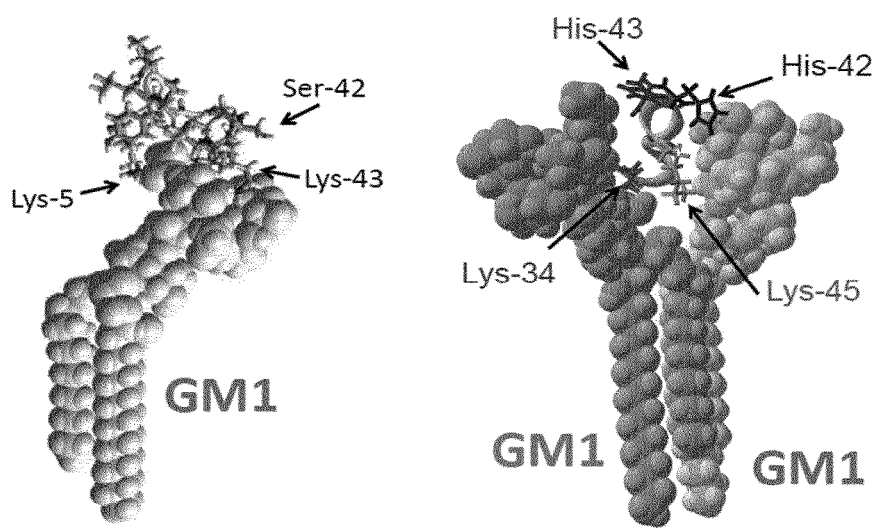

FIGS. 3A and 3B show molecular modeling of the wild-type and chimeric α-syn34-45 peptides.

A. Visualization of the positive electrostatic potential surface of the wild-type (left panel) or chimeric α-syn34-45/HH (right panel) peptides. B. Molecular modeling simulations of the wild-type (left panel) or chimeric α-syn34-45/HH (right panel) peptides interacting with a monomer or a dimer of ganglioside GM1.

Figure 4A:
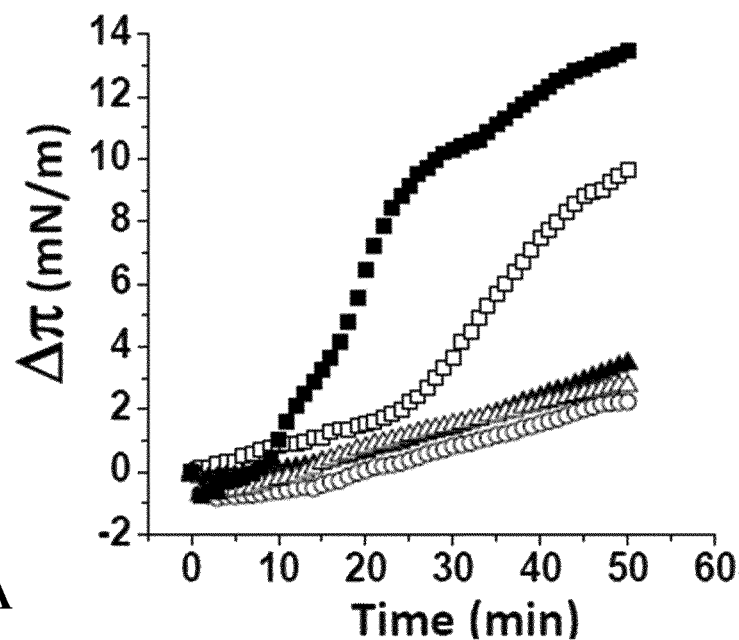
Figure 4B:
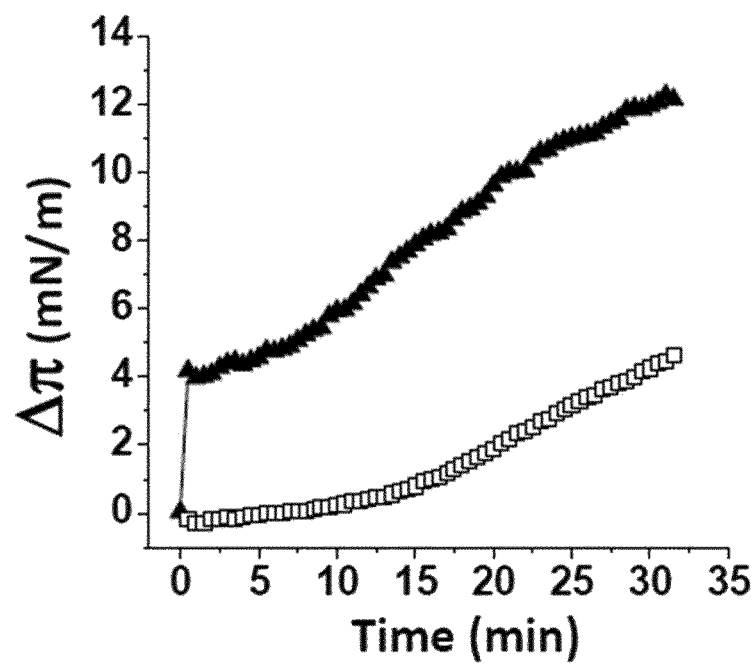

FIGS. 4A and 4B show experimental validation of the molecular modeling studies of α-syn34-45/HH-GM1 complex.

A. Interaction of the chimeric α-syn34-45/HH peptide with GD1a (full squares), GM1 (open squares), asialo-GM1 (full triangles), LacCer (open circles) and GlcCer (open triangles) in the monolayer assay (the experimental conditions were the same as those of FIG. 1A).

B. Interaction of α-syn34-45/HH with mixed monolayers of GM1:cholesterol or GM1:phosphatidylcholine (1:1, mol:mol).

Figure 4C:
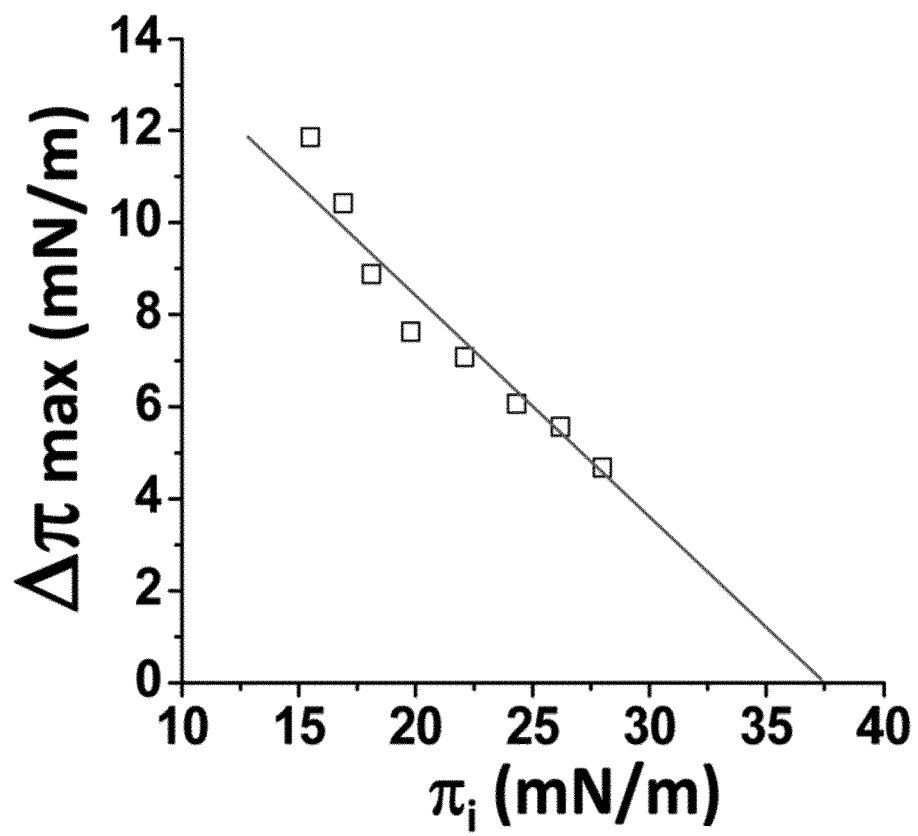

FIG. 4C: determination of the critical pressure of insertion of α-syn34-45/HH for GM1 monolayers. GM1 monolayers were prepared at various values of the initial surface pressure πi and probed with the chimeric α-syn34-45/HH peptide added in the aqueous subphase. The maximal surface pressure increase Δπmax was recorded at the equilibrium. The critical pressure of insertion πc (37.5 mN·m$^{-1}$) is determined as the intercept of the linear regression slope with the x-axis.

Figure 5:
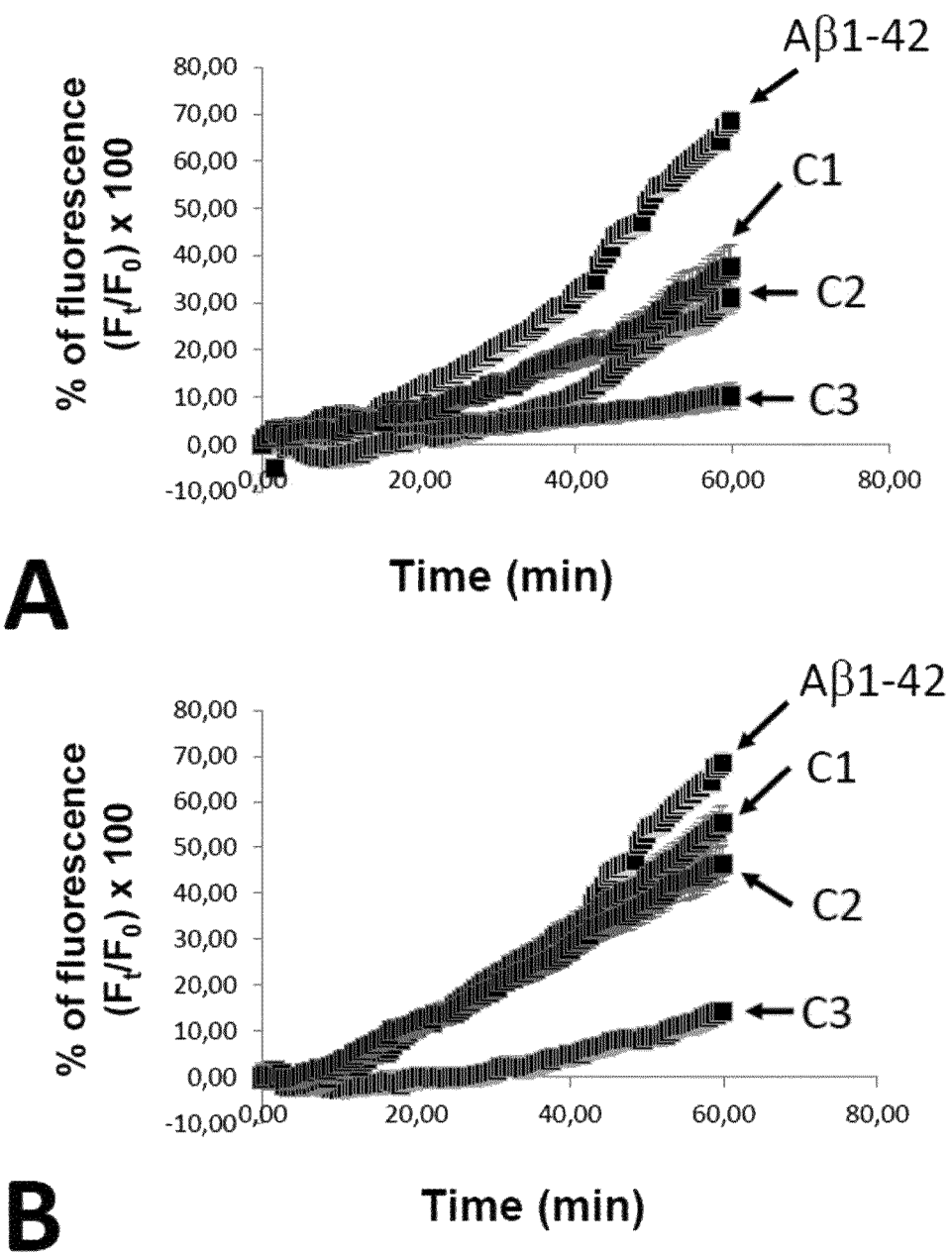

FIG. 5: Effect α-syn34-45/HH or α-syn34-45 on amyloid pore formation.

A. In a first experiment, SH-SY5Y cells were treated with Aβ1-42peptide (220 nM), and Ca$^{2+}$ dependent fluorescence was analyzed (top curve). In a second series of experiments, Aβ1-42 and the chimeric α-syn34-45/HH peptide (both 220 nM) were mixed extemporaneously directly injected onto the cells (C1 and C2 curves corresponding to two separate experiments). The C3 curve corresponds to the calcium response induced by the chimeric peptide alone. Results are expressed as mean±SD (n=100). In panel B, the same colors were used but the chimeric peptide was replaced by the wild-type α-syn34-45 peptide.

Figure 6:
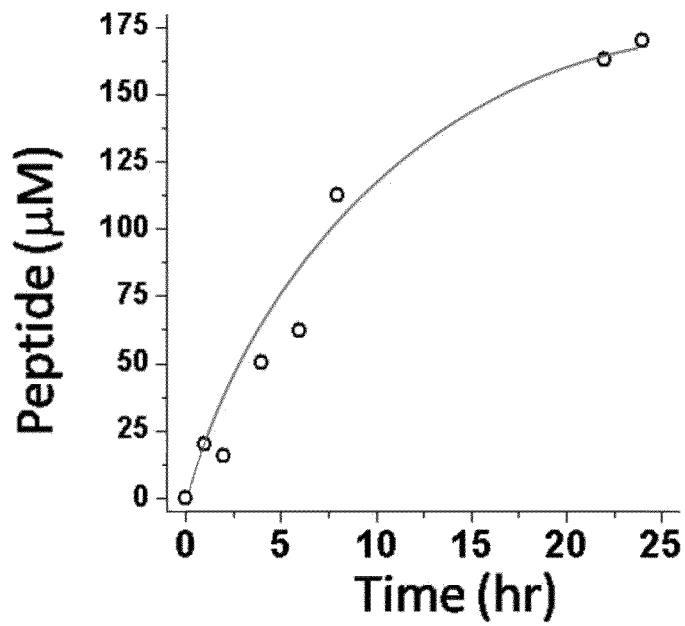

FIG. 6: Kinetics of transendothelial passage of the chimeric peptide α-syn34-45/HH through a monolayer of pure bEnd-3 cells. The cells were cultured on the filter of a two-compartment culture chamber until forming a tight monolayer with a transendothelial electrical resistance>100 Ω·cm$^2$. At time 0, the peptide (600 μM) was injected in the lower compartment and its appearance in the upper compartment was quantitatively determined by spectrophotometry.

Figure 7:
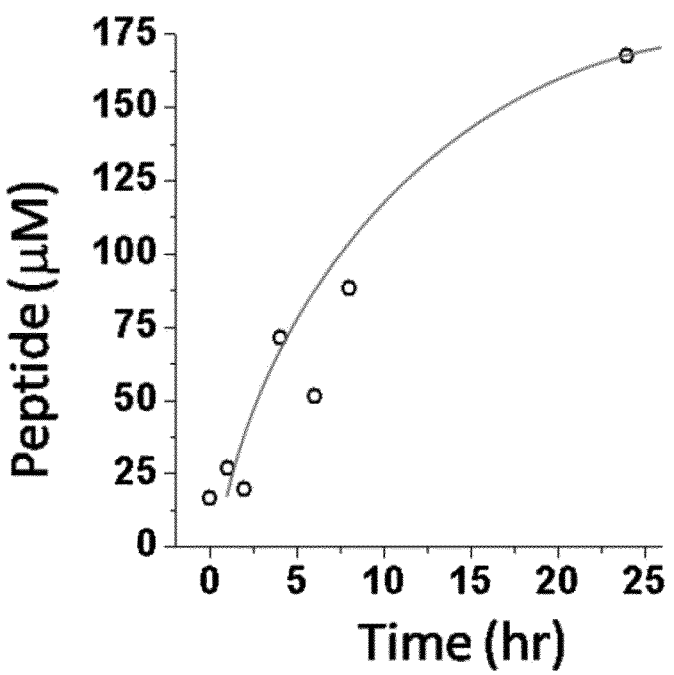

FIG. 7: Kinetics of transendothelial passage of the chimeric peptide α-syn34-45/HH through a monolayer of bEnd-3 cells that had been co-cultured with C6 cells. In this case bEnd-3 cells were cultured on the filter of a two-compartment culture chamber in presence of glial C6 cells cultured on the plastic wall of the lower compartment. When bEnd-3 cells had formed a tight monolayer with a transendothelial electrical resistance>100 Ω·cm$^2$, the filter was transferred in new culture plates and the experiment was then performed without C6 cells. At time 0, the peptide (600 μM) was injected in the lower compartment and its appearance in the upper compartment was quantitatively determined by spectrophotometry.

Figure 8:
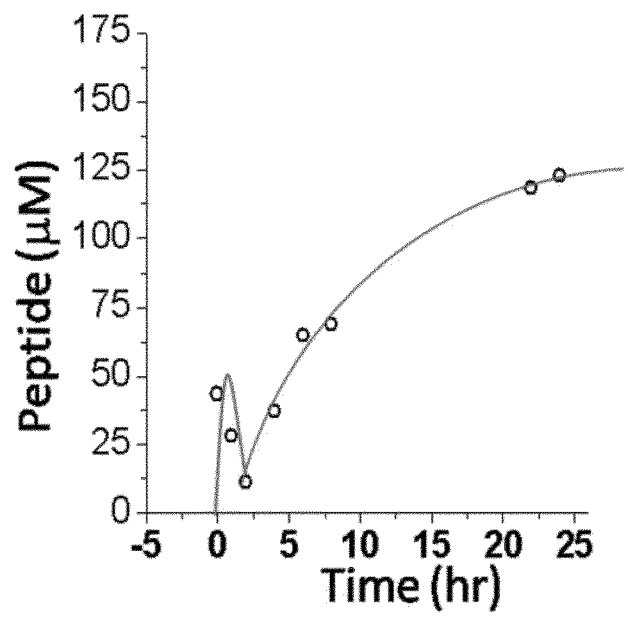

FIG. 8: Kinetics of transendothelial passage of the chimeric peptide α-syn34-45/HH through a monolayer of bEnd-3 cells that had been co-cultured with CTX cells. Same experiment as described in FIG. 7 but with bEnd3-cells initially co-cultured in presence of astrocytic CTX cells.

Figure 9:
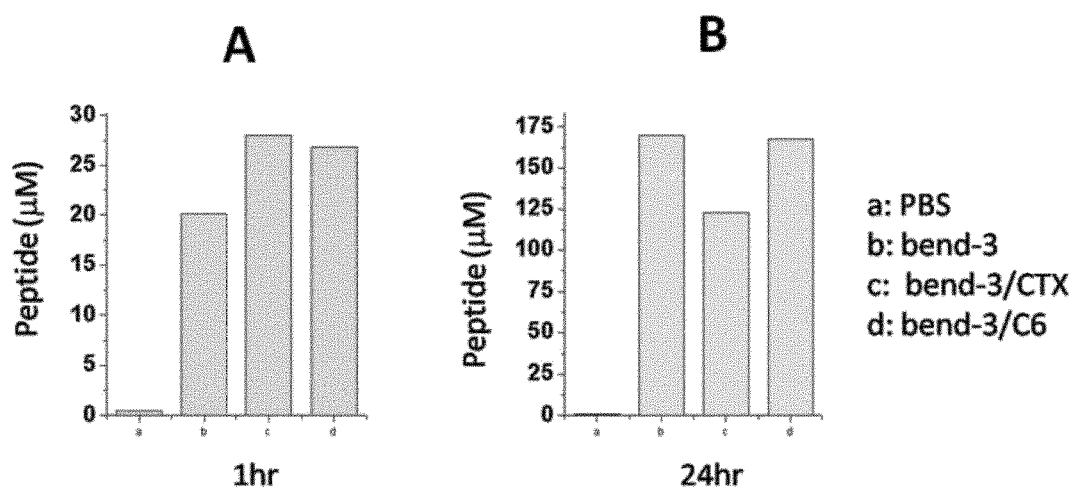

FIG. 9: Kinetics of transendothelial passage of the chimeric peptide α-syn34-45/HH through three in vitro models of the blood-brain barrier. The cellular models of the blood-brain barrier were: bEnd-3 cells alone (b), bEnd-3 cells co-cultured with C6 cells (c) or bEnd-3 cells co-cultured with C6 cells (d). A control experiment with no peptide added (a) was performed in parallel (in this case, the same volume of PBS was added to the cells). The histograms show the concentration of the chimeric peptide α-syn34-45/HH that has crossed the barrier after 1 hr (A) or 24 hr (B).

Figure 10:
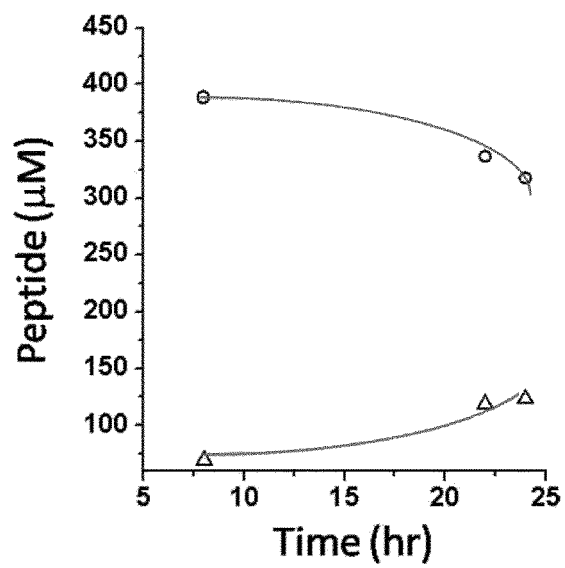

FIG. 10: Kinetics of transendothelial passage of the chimeric peptide α-syn34-45/HH through a monolayer of bEnd-3 cells. The upper curve shows the progressive disappearance of the peptide in the donor (i.e. lower) compartment. The lower curve shows the gradual appearance of the peptide in the acceptor (i.e. upper) compartment.

Figure 11:
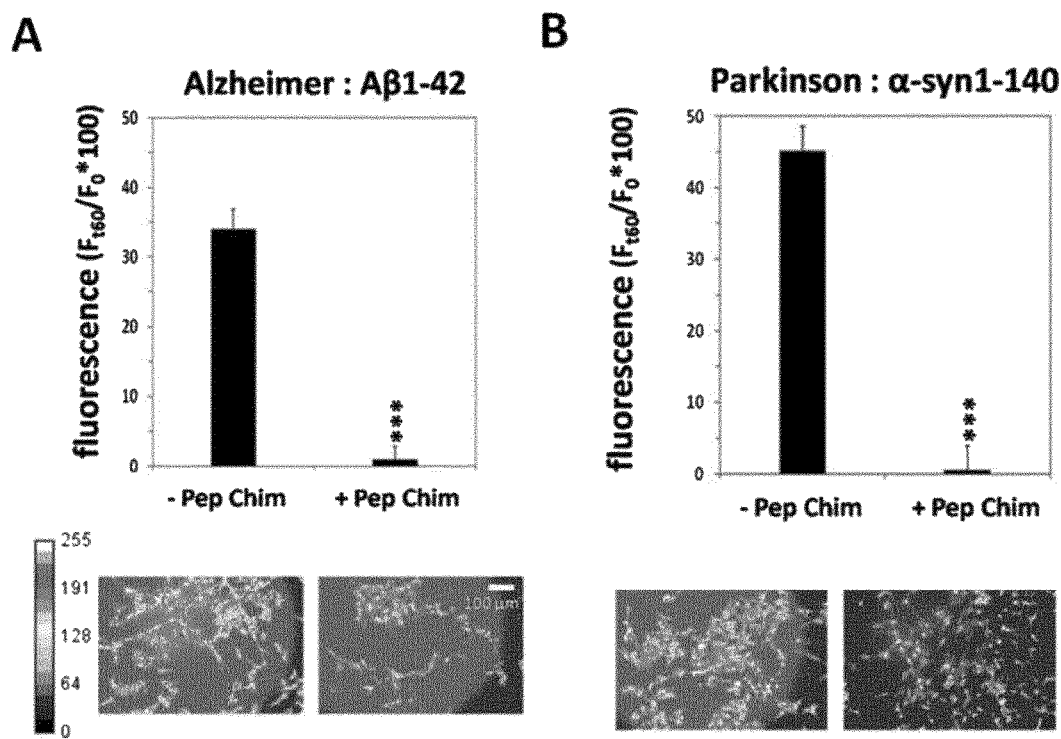

FIG. 11: Universal anti-Alzheimer and anti-Parkinson effect of the chimeric peptide α-syn34-45/HH on amyloid pore formation.

A. SH-SY5Y cells were treated with Aβ1-42 peptide (220 nM), and Ca$^{2+}$ dependent fluorescence was analyze. The histograms show the analysis of 100 cells (mean±SD). In absence of the chimeric peptide (− Pep Chim), amyloid pore formation induced by the Aβ1-42 peptide was evidenced by an increase of Ca$^{2+}$ fluorescence inside the cells. When Aβ1-42 was added to the cells in presence of the chimeric peptide α-syn34-45/HH (both 220 nM), there was no detectable increase of Ca$^{2+}$ fluorescence (+ Pep Chim). Representative microscopic fields of the cells treated with Aβ1-42 (left micrograph) or with Aβ1-42+chimeric peptide α-syn34-45/HH (right micrograph) are shown below the histograms. Warmer colors correspond to higher fluorescence (left scale).

B. Similar experiment performed with α-synuclein instead of Aβ1-42, in either the absence (− Pep Chim) or presence (+ Pep Chim) of chimeric peptide α-syn34-45/HH. ***, Significant difference; P<0.001.

Figure 12:
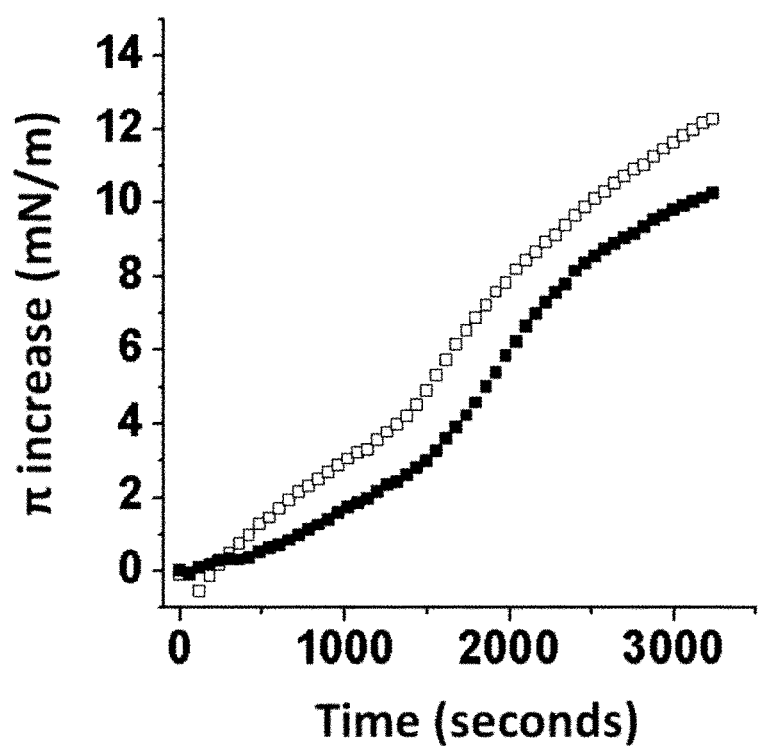

FIG. 12: Kinetics of interaction of chimeric peptide KEHHGVLYVGTK (SEQ ID NO: 11) (10 μM) with a monolayer of ganglioside GM1 (full squares) or GM3 (open squares). The interaction is measured by the increase in surface pressure (π) as a function of time following the addition of the peptide.

DETAILED DESCRIPTION OF THE INVENTION

The inventors have now shown that both Aβ and α-synuclein display a common, structurally-related glycolipid-binding domain with little sequence homology. The high affinity of Aβ for ganglioside GM1 is determined by the presence of a pair of histidine residues (His-13 and His-14). The inventors then replaced amino acids Ser-42 and Lys-43 of the minimal glycolipid-binding domain of α-synuclein (αsyn34-45) by two histidine residues. The resulting chimeric α-syn/HH peptide fully retained its ability to recognize ganglioside GM3 and has acquired the capacity to bind to condensed complexes of GM1 at high surface pressures.

The chimeric α-syn/HH peptide interacted almost exclusively with gangliosides, ignoring neutral glycolipids that are devoid of sialic acids (GalCer, LacCer, asialo-GM1).

The high affinity of the chimeric peptide of the invention for these gangliosides in their natural lipid environment, opens wide therapeutic applications.

Definitions

The term "patient" or "subject" refers to a human or non human animal, preferably a mammal, including male, female, adult and children.

As used herein, the term "treatment" or "therapy" includes curative and/or prophylactic treatment. More particularly, curative treatment refers to any of the alleviation, amelioration and/or elimination, reduction and/or stabilization (e.g., failure to progress to more advanced stages) of a symptom, as well as delay in progression of a symptom of a particular disorder.

Prophylactic treatment or "prevention" refers to any of: halting the onset, reducing the risk of development, reducing the incidence, delaying the onset, reducing the development, as well as increasing the time to onset of symptoms of a particular disorder. In the context of the present invention, the term "preventing" more particularly applies to a subject who is at risk of developing a particular disorder, ie any condition which involves gangliosides as cell surface receptor sites, including neurodegenerative disorders, infectious diseases, or tumors.

Two amino acid sequences are "homologous", "substantially homologous" or "substantially similar" when one or more amino acid residue are replaced by a biologically similar residue or when greater than 80% of the amino acids are identical, or greater than about 90%, preferably greater than about 95%, are similar (functionally identical). Preferably, the similar or homologous sequences are identified by alignment using, for example, the GCG (Genetics Computer Group, Program Manual for the GCG Package, Version 7, Madison, Wis.) pileup program, or any of the programs known in the art (BLAST, FASTA, etc.). Preferably, these homologous peptides do not include two cysteine residues, so that cyclization is prevented. Preferably the homologous sequences differ by mutations, such as substitutions, insertions and/or deletions of one or several amino acids. Preferably the homologous sequences differ only by conservative substitution(s).

The term "conservative substitution" as used herein denotes the replacement of an amino acid residue by another, without altering the overall conformation and function of the peptide, including, but not limited to, replacement of an amino acid with one having similar properties (such as, for example, polarity, hydrogen bonding potential, acidic, basic, shape, hydrophobic, aromatic, and the like). Amino acids with similar properties are well known in the art. For example, arginine, histidine and lysine are hydrophilic-basic amino acids and may be interchangeable. Similarly, isoleucine, a hydrophobic amino acid, may be replaced with leucine, methionine or valine. Neutral hydrophilic amino acids, which can be substituted for one another, include asparagine, glutamine, serine and threonine.

A "ganglioside" refers to a molecule composed of a glycosphingolipid (ceramide and oligosaccharide) with one or more sialic acids (e.g. n-acetylneuraminic acid, NANA) linked on the sugar chain. NeuNAc, an acetylated derivative of the carbohydrate sialic acid, makes the head groups of gangliosides anionic at pH 7. Gangliosides are present and concentrated on cell surfaces, with the two hydrocarbon chains of the ceramide moiety embedded in the plasma membrane and the oligosaccharides located on the extracellular surface, where they present points of recognition for extracellular molecules or surfaces of neighboring cells. Structures of common gangliosides (GM1, GM2, GM3, GD1a, GD1b, GD2, GD3, GT1b, GQ1) are known in the art.

Chimeric Peptide of the Invention:

The present invention provides a peptide comprising amino acid sequence E-$X_1X_2X_3$-YVGHH-$X_4$ (SEQ ID NO: 9), preferably EGVLYVGHHT (SEQ ID NO: 1).

The invention further provide proteolysis-resistant peptides which show a sequence deriving from SEQ ID NO: 1 to SEQ ID NO: 9, by one or more chemical modifications that protect the peptide against proteolysis, e.g. as defined below.

Substantially homologous peptides, which show a sequence deriving from SEQ ID NO: 1 to SEQ ID NO: 9 by one or more conservative substitutions, are further encompassed in the present invention.

All the peptides of the invention comprise two consecutive histidine residues.

The peptide of the invention preferably has between 10 and 30 amino acids, still preferably between 12 and 20, preferably between 12 and 16 amino acids.

Advantageously, both N-term and C-term amino acids are basic amino acids, preferably independently selected from the group consisting of lysine, arginine, and histidine.

In a particular embodiment, the peptide comprises or consists of $X_5$-EGVLYVGHHT-$X_6$ (SEQ ID NO: 2), wherein $X_5$ and $X_6$ are independently lysine, arginine, or histidine.

A preferred peptide consists of KEGVLYVGHHTK (SEQ ID NO: 3).

Other peptides comprise or consist of
REGVLYVGHHTR (SEQ ID NO: 6);
REGVLYVGHHTK (SEQ ID NO: 7);
KEGVLYVGHHTR (SEQ ID NO: 8).

Reversed Peptides:

Peptides in which the pair of Histidine residues is moved at the N-terminal part of the chimeric peptide are further described.

Such peptides, herein also designated "reversed" chimeric peptides, are 10 to 30 aminoacids long.

Such peptides comprise or consist of $X_5$-EHHGVLYVGT-$X_6$ (SEQ ID NO: 10), wherein $X_5$ and $X_6$ are independently lysine, arginine, or histidine.

A particular peptide is KEHHGVLYVGTK (SEQ ID NO:11).

The below sections apply to these reversed peptides as well as all chimeric peptides herein described. These reversed peptides display the ganglioside-binding properties of both α-synuclein and β-amyloid peptide. These peptides, or the nucleic acids coding for the peptides, are thus also described for preventing or treating any condition which involves gangliosides as cell surface receptor sites, including neurodegenerative disorders, infectious diseases, or tumors.

Peptide Preparation:

Peptides described herein can be synthesized using standard synthetic methods known to those skilled in the art, for example chemical synthesis or genetic recombination. In a preferred embodiment, peptides are obtained by stepwise condensation of amino acid residues, either by condensation of a preformed fragment already containing an amino acid sequence in appropriate order, or by condensation of several fragments previously prepared, while protecting the amino acid functional groups except those involved in peptide bond during condensation. In particular, the peptides can be synthesized according to the method originally described by Merrifield.

Examples of chemical synthesis technologies are solid phase synthesis and liquid phase synthesis. As a solid phase synthesis, for example, the amino acid corresponding to the C-terminus of the peptide to be synthesized is bound to a support which is insoluble in organic solvents, and by alternate repetition of reactions, one wherein amino acids with their amino groups and side chain functional groups protected with appropriate protective groups are condensed one by one in order from the C-terminus to the N-terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoc (t-butoxycarbonyl), Cl—Z (2-chlorobenzyloxycarbonyl), Br—Z (2-bromobenzyloyycarbonyl), Bzl (benzyl), Fmoc (9-fluorenylmethoxycarbonyl), Mbh (4,4'- dimethoxydibenzhydryl), Mtr (4-methoxy-2,3,6-trimethyl-benzenesulphonyl), Trt (trityl), Tos (tosyl), Z (benzyloxycarbonyl) and Clz-Bzl (2,6-dichlorobenzyl) for the amino groups; NO2 (nitro) and Pmc (2,2, 5,7, 8-pentamethylchromane-6-sulphonyl) for the guanidino groups); and tBu (t-butyl) for the hydroxyl groups). After synthesis of the desired peptide, it is subjected to the de-protection reaction and cut out from the solid support. Such peptide cutting reaction may be carried with hydrogen fluoride or tri-fluoromethane sulfonic acid for the Boc method, and with TFA for the Fmoc method.

Alternatively, the peptide may be synthesized using recombinant techniques. In this case, a nucleic acid and/or a genetic construct comprising or consisting of a nucleotide sequence encoding a peptide according to the invention, polynucleotides with nucleotide sequences complementary to one of the above sequences and sequences hybridizing to said polynucleotides under stringent conditions.

The invention further relates to a genetic construct consisting of or comprising a polynucleotide as defined herein, and regulatory sequences (such as a suitable promoter(s), enhancer(s), terminator(s), etc.) allowing the expression (e.g. transcription and translation) of a peptide according to the invention in a host cell.

Thus, in another aspect, the invention relates to a host or host cell that expresses (or that under suitable circumstances is capable of expressing) a peptide of the invention; and/or that contains a polynucleotide of the invention or genetic construct of the invention.

The method of producing the peptide may optionally comprise the steps of purifying said peptide, chemically modifying said peptide, and/or formulating said peptide into a pharmaceutical composition.

Further Protection Against Proteolysis:

The N- and C-termini of the peptides described herein may be optionally protected against proteolysis. For instance, the N-terminus may be in the form of an acetyl group, and/or the C-terminus may be in the form of an amide group. Internal modifications of the peptides to be resistant to proteolysis are also envisioned, e.g. wherein at least a —CONH— peptide bond is modified and replaced by a (CH2NH) reduced bond, a (NHCO) retro-inverso bond, a (CH2-O) methylene-oxy bond, a (CH2-S) thiomethylene bond, a (CH2CH2) carba bond, a (CO—CH2) cetomethylene bond, a (CHOH—CH2) hydroxyethylene bond), a (N—N) bound, a E-alcene bond or also a —CH═CH-bond.

For instance the peptide may be modified by acetylation, acylation, amidation, cross-linking, cyclization, disulfide bond formation, formation of covalent cross-links, formation of cysteine, formation of pyroglutamate, formylation, gamma-carboxylation, glycosylation, GPI anchor formation, hydroxylation, iodination, methylation, myristylation, oxidation, phosphorylation, and the like.

The peptides of the invention may be composed of amino acid(s) in D configuration, which render the peptides resistant to proteolysis. They may also be stabilized by intramolecular crosslinking, e.g. by modifying at least two amino acid residues with olefinic side chains, preferably C3-C8 alkenyl chains, preferably penten-2-yl chains) followed by chemical crosslinking of the chains, according to the so-called "staple" technology described in Walensky et al, 2004. For instance, amino acids at position i and i+4 to i+7 can be substituted by non-natural aminoacids that show reactive olefinic residues. All these proteolysis-resistant chemically-modified peptides are encompassed in the present invention.

In another aspect of the invention, peptides are covalently bound to a polyethylene glycol (PEG) molecule by their C-terminal terminus or a lysine residue, notably a PEG of 1500 or 4000 MW, for a decrease in urinary clearance and in therapeutic doses used and for an increase of the half-life in blood plasma. In yet another embodiment, peptide half-life is increased by including the peptide in a biodegradable and biocompatible polymer material for drug delivery system forming microspheres. Polymers and copolymers are, for instance, poly(D,L-lactide-co-glycolide) (PLGA) (as illustrated in US2007/0184015, SoonKap Hahn et al).

In other embodiments, the peptides of the invention may be protected by dendrimers or other branched molecules, or by nanoparticles or nanocarriers, which may encapsulate them or to which they may be optionally coupled.

Nucleic Acids

The invention also relates to a polynucleotide comprising or consisting of a nucleotide sequence encoding a peptide according to the invention.

The invention further relates to a genetic construct consisting of or comprising a polynucleotide as defined herein, and regulatory sequences (such as a suitable promoter(s), enhancer(s), terminator(s), etc.) allowing the expression (e.g. transcription and translation) of a peptide according to the invention in a host cell.

The genetic constructs of the invention may be DNA or RNA, preferably cDNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In a preferred but non-limiting aspect, a genetic construct of the invention comprises i) at least one nucleic acid of the invention; operably connected to ii) one or more regulatory elements, such as a promoter and optionally a suitable terminator; and optionally also iii) one or more further elements of genetic constructs such as 3'- or 5'-UTR sequences, leader sequences, selection markers, expression markers/reporter genes, and/or elements that may facilitate or increase (the efficiency of) transformation or integration.

The nucleic acid may especially be carried by a viral vector, such as an adenovirus or a lentivirus, for ex vivo or in vivo infection and expression of the peptide of the invention.

Therapeutic Applications:

The peptide or nucleic acid as defined herein is useful as a medicament.

It is herein provided a method for preventing or treating a condition which involves adhesion to a cell membrane ganglioside, in a patient, which method comprises administering said patient with an effective amount of a peptide of the invention, or of a nucleic acid encoding such peptide. In a preferred embodiment, it is provided a method for preventing or treating a neurodegenerative disorder in a patient, which method comprises administering said patient with an effective amount of a peptide of the invention, or of a nucleic acid encoding such peptide.

The neurodegenerative disorder includes Alzheimer's disease (AD), Parkinson's disease (PD), Creutzfeldt-Jakob Disease (CJD), which are all known to involve adhesion to GM1 and/or GM3 gangliosides.

The neurodegenerative disorder may also be Guillain-Barré syndrome, which involves GM1 and GD1a gangliosides. In another embodiment, it is provided a method for preventing or treating an infectious disease in a patient, which method comprises administering said patient with an effective amount of a peptide of the invention, or a nucleic acid encoding such peptide. Generally speaking, all pathogenic microorganisms seem to use gangliosides as receptor sites at the surface of the infected cells.

The infectious disease is advantageously an infection by a virus, e.g. HIV, influenza virus, HCV, HBV, rotavirus, BK virus, Ebola virus, or an infection by bacteria, e.g. *Helicobacter pylori*, or *Mycoplasma pneumonia*. The infectious disease may involve bacterial toxins, such as *Escherichia coli, Clostridium tetani, Clostridium botulinum, Clostridium perfringens*, or *Vibrio cholerae*. Prion diseases are also encompassed, as well as infections by parasites, such as *Plasmodium falfciparum* (which involves adhesion to GM1a).

The skilled person can measure interactions between proteins of the microorganism (such as surface glycoproteins of virus, e.g. gp120 of HIV-1) and cell membrane gangliosides (e.g. GM3), and inhibition of these interactions by the chimeric peptide of the invention. For that purpose, the gangliosides can be exposed at the surface of an aqueous phase to form a lipid monolayer at the water-air interface. The microorganism proteins are then injected in the aqueous subphase and their interaction with the gangliosides is determined by measuring superficial tension. Infection tests can further be conducted, to confirm the ability of the peptide to block the infection.

In still another embodiment, it is provided a method for preventing or treating a tumor in a patient, which method comprises administering said patient with an effective amount of a peptide of the invention, a nucleic acid encoding such peptide.

The functions of gangliosides as specific determinants indeed suggest its important role in the growth and differentiation of tissues as well as in carcinogenesis. See also Daniotti et al, 2013 for a review of tumor-associated gangliosides.

The anti-tumor therapy of the invention is helpful in eradicating any persistent microscopic malignancy, and/or preventing or delaying relapses.

Furthermore, the peptide (or nucleic acid encoding such peptide) may be used for preventing or treating metastases.

The peptide of the invention (or nucleic acid encoding such peptide) is indeed particularly useful in preventing spread or proliferation of metastatic cells, in particular through blood-brain barrier.

The tumor may be cancer, such as a solid cancer or a haematologic cancer. In a preferred embodiment, the tumor is selected from the group consisting of melanoma, neuroblastoma, glioma, small cell lung cancer, non-small cell lung cancer, T-cell acute lymphocytic leukemia, adult T-cell leukemia, breast carcinoma, renal carcinoma.

Pharmaceutical Compositions:

The peptides of the invention (or nucleic acid encoding such peptide) may be administered by any convenient route including intravenous, oral, transdermal, subcutaneous, mucosal, intramuscular, intrapulmonary, intranasal, parenteral, rectal, vaginal and topical.

The peptides are formulated in association with a pharmaceutically acceptable carrier.

It is thus provided a pharmaceutical composition comprising a peptide as defined above (or nucleic acid encoding such peptide), in association with a pharmaceutically-acceptable carrier.

The pharmaceutical composition may also include any other active principle.

The preparation of a pharmacological composition that contains active ingredients dissolved or dispersed therein is well understood in the art and need not be limited based on formulation. Typically such compositions are prepared as injectables either as liquid solutions or suspensions; however, solid forms suitable for solution, or suspensions, in liquid prior to use can also be prepared. The preparation can also be emulsified. In particular, the pharmaceutical compositions may be formulated in solid dosage form, for example capsules, tablets, pills, powders, dragees or granules.

The choice of vehicle and the content of active substance in the vehicle are generally determined in accordance with the solubility and chemical properties of the active compound, the particular mode of administration and the provisions to be observed in pharmaceutical practice. For example, excipients such as lactose, sodium citrate, calcium carbonate, dicalcium phosphate and disintegrating agents such as starch, alginic acids and certain complex silicates combined with lubricants such as magnesium stearate, sodium lauryl sulphate and talc may be used for preparing tablets. To prepare a capsule, it is advantageous to use lactose and high molecular weight polyethylene glycols. When aqueous suspensions are used they can contain emulsifying agents or agents which facilitate suspension. Diluents such as sucrose, ethanol, polyethylene glycol, propylene glycol, glycerol and chloroform or mixtures thereof may also be used.

Preparation can involve the formulation of the desired molecule with an agent, such as injectable microspheres, bio-erodible particles, polymeric compounds (such as polylactic acid or polyglycolic acid), beads or liposomes, which may provide controlled or sustained release of the product.

In a particular embodiment, the peptide (or nucleic acid encoding such peptide) may be administered by electroporation. Electroporation, also known as electropermeabilization or electroinjection, is the permeabilization of cell membranes as a consequence of the application of certain short and intense electric fields across the cell membrane, the cells or the tissues.

The dosing is selected by the skilled person and depends on the route of administration and the dosage form that is used. Total daily dose of peptides administered to a subject in single or divided doses may be in amounts, for example, of from about 0.001 to about 100 mg/kg body weight daily and preferably 0.01 to 10 mg/kg/day. A daily dosage of about 5 mg/kg is preferred. Dosage unit compositions may contain such amounts of such submultiples thereof as may be used to make up the daily dose. It will be understood, however, that the specific dose level for any particular patient will depend upon a variety of factors including the body weight, general health, sex, diet, time and route of administration, rates of absorption and excretion, combination with other drugs and the severity of the particular disease being treated.

Preferably the peptide is administered once a day during a period of at least one week, preferably at least two weeks.

Further aspects and advantages of the present invention will be disclosed in the following experimental section, which should be regarded as illustrative and not limiting the scope of the present application.

EXAMPLES

Example 1: Interaction of the Chimeric Peptide of the Invention with Cell-Membrane Gangliosides Materials and Methods Materials.

Synthetic peptides with a purity >95% were obtained from Schafer-N (Copenhagen, Denmark). Ultrapure apyrogenic water was from Biorad (Marnes La Coquette, France). All lipids were purchased from Matreya (Pleasant Gap, Pa.).

Molecular Modeling.

In silico studies of peptide-ganglioside interactions were performed with the Hyperchem 8 program (ChemCAD, Obernay, France) as described (Fantini and Yahi, 2011a). The molecules were visualized with Hyperchem 8, PDB-viewer (Guex et al, 1997) and Molegro Molecular Viewer (Thomsen et al, 2006) softwares.

Lipid Monolayer Assay.

Peptide-cholesterol interactions were studied with the Langmuir film balance technique using a Kibron microtensiometer as previously described (Fantini and Yahi, 2011a).

Calcium Measurements.

Cells were plated in 35 mm culture dishes, grown during 72 h and loaded with 5 µM Fluo-4 AM (Invitrogen-Life Technologies, Saint Aubin, France) for 30 min in the dark, washed three times with HBSS (Gibco-Life Technologies, Saint-Aubin, France), and incubated for 20 min at 37° C. The calcium fluxes were estimated by measuring the variation of cell fluorescence intensity after peptide injection into the recording chamber directly above an upright microscope objective (BX51W Olympus, Rungis, France) equipped with an illuminator system MT20 module. Fluorescence emission at 525 nm was imaged by a digital camera CDD (ORCA-ER Hamanatsu, Japan) after fluorescence excitation at 490 nm. Times-lapse images (1 frame/10 s) were collected using the CellR Software (Olympus). Signals were expressed as fluorescence after treatment (Ft) divided by the fluorescence before treatment (F0) multiplied by 100. The results are averaged and the percentage of fluorescence of control is subtracted for each value, as described previously (Di Scala et al, 2014; Fantini et al, 2014).

Results

The amino acid sequences of the minimal glycolipid-binding domain of α-synuclein and Aβ are indicated below:

```
Human α-synuclein 34-45:
                                        (SEQ ID NO: 4)
KEGVLYVGSKTK Human Aβ5-16:
                                        (SEQ ID NO: 5)
RHDSGYEVHHQK Chimeric α-syn34-45/HH:
                                        (SEQ ID NO: 3)
KEGVLYVGHHTK
```

Replacing the two histidine residues in Aβ5-16 by alanine resulted in a total loss of interaction with GM1 (FIG. 1A). In this experiment, a monolayer of ganglioside GM1 was prepared at the air-water interface and the peptide was injected in the aqueous subphase. The interaction of the peptide with the ganglioside was evidenced by an increase in the surface pressure of the monolayer, which was followed in real-time with a platinum probe (see Thakur et al, 2009 for a full description of the technique and its application to amyloid proteins). For the wild-type Aβ5-16 peptide, the surface pressure started to increase immediately after the injection of the peptide, reaching a maximum after 30 minutes of incubation. In contrast, the double mutant His-13Ala/His-14Ala did not interact with GM1 (FIG. 1A). Then single mutants were assayed to identify which of the two His is actually critical for GM1 recognition. Surprisingly, both appeared to be involved, since a total loss of interaction was observed for each single mutant (His-13Ala and His-14Ala). Molecular modeling simulations shed some light on this result (FIG. 1B). The formation of a stable complex between Aβ5-16 and GM1 required two GM1 molecules forming a chalice-like receptacle for the peptide. In this model, His-13 interacted with one GM1, and His-14 with the second one. Clearly, the cooperation between both GM1 molecules allowed an optimal interaction with the Aβ5-16 peptide driven by histidine residues. Conversely, because it is devoid of these histidine residues, the glycolipid-binding domain of α-synuclein (α-syn34-45) has a marked preference for ganglioside GM3 instead of GM1.

Given the critical role of histidine residues for the high affinity interaction of Aβ5-16 with the GM1 dimer, the inventors decided to introduce a similar pair of adjacent His residues in α-syn34-45 and synthesized a chimeric α-syn34-45Ser-42His/Lys-43His (referred to as α-syn/HH, FIG. 1C). Since neither Ser-42 nor Lys-43 appeared to be involved in GM3 binding, the inventors surmised that this double mutation would not interfere with the interaction of the chimeric α-syn/HH peptide with a monolayer of GM3. As shown in FIG. 2, the α-syn/HH peptide behaved exactly as predicted. Its kinetic of interaction with GM3 was exactly the same as the wild-type α-syn34-45 peptide (FIG. 2A) and the critical pressure of insertion (πc) was estimated to 37.5 mN·m$^{-1}$ for both the wild-type and chimeric peptides (FIG. 2B). πc is proportional to the binding affinity; this parameter corresponds to the surface pressure of the monolayer above which no interaction occurs because the glycolipids are too densely packed (Thakur et al, 2009; Fantini et al, 2011b). Thus, the introduction of the pair of His residues in α-syn34-45 did not interfere at all with the GM3-binding capability of the peptide. In contrast, the chimeric α-syn/HH peptide has gained a marked increase of affinity for GM1, which was clearly observed in real-time kinetics studies (FIG. 2C).

Moreover, the value of πc measured with GM1 monolayers increased from 25 mN·m$^{-1}$ for the wild-type α-syn34-45 peptide to 37.5 mN·m$^{-1}$ in the case of α-syn/HH, which indicates a significant stronger affinity of the chimeric peptide for GM1 (FIG. 2D).

In silico analysis of the wild-type and α-syn/HH peptides indicated that they occupy the same molecular volume. Yet the introduction of the pair of His residues in the α-syn/HH peptide resulted in a more symmetrical distribution of the electrostatic potential (FIG. 3A). Thus, the wild-type α-syn34-45 and the chimeric α-syn/HH peptides greatly differed in the way they interacted with the anionic glycone headgroup of GM1. As shown in FIG. 3B (left panel), α-syn34-45 adopted a curved form around the protruding sugar part of a monomer of GM1. Because of its more balanced distribution of the electrostatic field, the chimeric peptide, could form a stable complex with a dimer of GM1 molecules arranged in a typical chalice-like receptacle (FIG. 3B, right panel). As for the Aβ5-16/GM1 complex, each of the His residues of α-syn/HH interacted with its own GM1 ganglioside, in a way that could be compared to the wings of a butterfly on the chalice of a flower. A detailed description of the molecular interactions between α-syn/HH and the GM1 dimer is given in FIG. 1C. Overall, these data strongly support the notion that the His residues are critical for recruiting the GM1 molecules into a functional chalice-shaped dimer able to accommodate the glycolipid-binding domain of amyloid proteins.

Several experiments were conducted to validate this conclusion. First the inventors analyzed the interaction of the α-syn/HH peptide with a series of glycolipids. As a matter of fact, this chimeric peptide displayed a selective affinity for gangliosides (GM1, GM3, GM4, GD1a, GD3 and GT1b) and reacted very poorly with neutral glycolipids (GalCer, LacCer, asialo-GM1) (FIG. 4A and Table 1).

TABLE 1

Ganglioside specificity of wild-type α-syn34-45
and chimeric α-syn34-45/HH peptides.

| Ganglioside | α-syn34-45 | α-syn34-45/HH (SEQ ID NO: 3) |
|---|---|---|
| GM1 | + | +++ |
| GM3 | +++ | +++ |
| GM4 | + | +++ |
| GD1a | + | +++ |
| GD3 | + | +++ |
| GT1b | + | +++ |

All interactions were measured with ganglioside monolayers.
The peptides were added in the aqueous subphase at a concentration 10 μM.
(+) means a critical pressure of insertion <25 mN · m$^{-1}$ and (+++) a critical pressure of insertion >25 mN · m$^{-1}$.

This indicates that the presence of at least one sialic in the glycone part of the glycolipid is required for binding, in full agreement with the molecular modeling data (FIG. 1C). Then the inventors analyzed the impact of the lipid environment on the interaction between GM1 and the chimeric α-syn/HH peptide. In this experiment, the inventors prepared mixed monolayers of GM1/cholesterol and GM1/phosphatidylcholine and followed the kinetics of interaction of α-syn/HH with these monolayers. As shown in FIG. 4B, cholesterol considerably accelerated the interaction of α-syn/HH peptide with GM1, whereas phosphatidylcholine rather tended to slow down the reaction. This is in line with the well-known effect of cholesterol to form condensed complexes with GM1 (Radhakrishnan et al, 2000), allowing a sterol control on glycolipid conformation (Yahi et al, 2001; Lingwood et al, 2011). Moreover, the interaction of cholesterol with GM1 has been shown to stabilize the chalice-like conformation of GM1 dimers (Fantini et al, 2013). In this respect, cholesterol is expected to speed up the interaction without increasing the affinity of the α-syn/HH for GM1 (the active conformation can be achieved without cholesterol, but with a delayed kinetics, as shown in FIG. 4B). The experimental determination of πc for mixed GM1/cholesterol monolayers (37.5 mN·m$^{-1}$) strongly supports this view (FIG. 4C).

When the neurotoxic Aβ1-42 peptide was incubated with human neuroblastoma SH-SY5Y cells pre-loaded with the fluorescent-sensitive dye Fluo-4 AM, a dramatic increase of intracellular Ca$^{2+}$ levels was observed (FIG. 5). This elevation of Ca$^{2+}$ levels induced was significantly reduced in presence of equimolar amounts of the chimeric α-syn/HH peptide (FIG. 5A). This effect was highly dependent on the presence of the couple of His residues, since in comparison the wild-type chimeric α-syn34-45 peptide, had only very little inhibitory activity (FIG. 5B). This is consistent with the prominent role played by GM1, and not GM3, in the neurotoxicity of Alzheimer's β-amyloid peptides (Fantini et al, 2010; Fantini et al, 2013). Finally, one should note the chimeric α-syn/HH peptide by itself had little effect on Ca$^{2+}$ fluxes, indicating a lack of intrinsic neurotoxicity.

Example 2: Transport Through the Blood-Brain Barrier

In order to study the transport of the chimeric peptide α-syn34-45/HH: KEGVLYVG<u>HH</u>TK (SEQ ID NO: 3) through the blood-brain barrier (BBB) the inventors have reconstituted a functional cellular system based on a monolayer of endothelial cells (murine bEnd-3 cells, ATCC #CRL-2299). These cells are plated at various densities ranging from 10.000 to 50.000 cells per well in two-compartment cell chambers (Greiner Bio-one). The lower compartment of the chamber is a well that is part of 12-well culture plate. The upper chamber is equipped with a permeable filter (mean pore diameter of 0.4 μm) onto which the cells are seeded. The cells are cultured in DMEM/F12 10% fetal calf serum.

At confluency, the cells formed a uniform monolayer with a transendothelial resistance of 150-200 Ω·cm$^2$ (measured with the EVOM apparatus, WPI). The transendothelial resistance reflects the presence of tight junctions overall the culture. These tight junctions efficiently prevent the paracellular passage of molecules. It is considered that the endothelium is tight when this value is >100 Ω·cm$^2$. Therefore, all experiments are performed with functional endothelial barriers.

Three models of barriers have been used: i) monolayers of pure bend-3 cells, ii) monolayers of bEnd-3 cells co-cultured with astrocytic CTX-TNA2 cells (ATCC #CRL-2006) plated in the lower compartment of the culture chambers, and iii) monolayers of bend-3 cells co-cultured with glial C6 cells (ATCC #CCL-107) plated in the lower compartment of the culture chambers. The rationale for using co-culture system is to improve the differentiation of the reconstituted endothelium due to the secretion of trophic factors by the glial cells. In all cases, the values of transendothelial resistance in these different culture systems were always above 150-200 Ω·cm$^2$.

Typical values of transendothelial resistance are:
pure bEnd-3 monolayers: 185 Ω·cm$^2$.
bEnd-3/CTX-TNA2: 153 Ω·cm$^2$.
bEnd-3/C6: 186 Ω·cm$^2$.

The chimeric peptide was injected in the lower compartment of the culture chambers and its concentration in both the lower and upper compartments was analyzed as a function of time.

The passage of the peptide through the endothelial barrier is thus followed in real-time. The concentration of the chimeric peptide is determined by spectrophotometry. An aliquot of 2 μL was harvested from the culture media at different times following the addition of the peptide, so that at the end of the experiment the whole volume harvested was <10% of the initial volume. A whole spectrum of the peptide was performed to determine the A230/A275 ratio that displays the characteristic value of 6 (the peptide has 11 peptide bonds that absorb at 230 nm and a tyrosine residues with a peak at 275 nm).

2.1. Kinetics of Passage Through a Pure Bend-3 Barrier.

In this experiment the peptide was injected underneath a tight monolayer of pure bend-3 cells with a mean transendothelial resistance of 185 Ω·cm$^2$. The cells were rinsed twice in PBS-Ca$^{2+}$ and then incubated with no peptide (upper compartment, PBS-Ca$^{2+}$ alone) or 600 μM of chimeric peptide (lower compartment). The use of a calcium-containing buffer such as PBS-Ca$^{2+}$ was necessary to maintain the integrity of tight junctions throughout the experiment (after 24 hr of incubation, the transendothelial resistance was still as high as 162 Ω·cm$^2$). Thus the peptide did not induce any toxicity to the endothelial cells and, most importantly, did not affect the barrier function of the cells through a direct effect on tight junctions).

The chimeric peptide gradually appeared in the upper compartment as assessed by the spectrophotometric analysis.

The A230/A275 ratio was equal to 6 for all spectra, which indicated that the chimeric peptide—and not cellular proteins—were indeed recovered from the upper compartment. The kinetics of passage of the chimeric peptide through the endothelial barrier is on FIG. 6.

2.2. Kinetics of Passage Through a bEnd-3/C6 Barrier.

Similar data were obtained with the bEnd-3/C6 system. In this case, the bend-3 cells were co-cultured for 6 days in presence of C6 cells plated in the lower compartment of the culture chambers. For the experiment, the upper compartments were transferred into a new plate so that the co-cultured glial cells were not present during the transport analysis. In fact, the co-cultured cells were present only during the growth and differentiation of bEnd-3 cells.

In this co-culture system, the values of the transendothelial resistance were 186 Ω·cm$^2$ at t$_o$ (time of peptide injection) and 152 Ω·cm$^2$ after 24 hours of incubation with peptide. Therefore, the presence of the peptide did not significantly affect the functionality of tight junctions since the transendothelial resistance remained >100 Ω·cm$^2$.

The peptide concentrations recovered in the upper compartment are presented on FIG. 7.

2.3. Kinetics of Passage Through a bEnd-3/CTX-TNA2 Barrier.

Finally the inventors have studied the transendothelial passage of chimeric peptide through the bend-3/CTX system. In this case, the bEnd-3 cells were co-cultured for 6 days in presence of CTX-TNA2 cells plated in the lower compartment of the culture chambers. The, the upper compartments were transferred into a new plate and the experiment was performed as indicated in paragraph 2 (bEnd-3/C6 system).

In this case, the values of the transendothelial resistance were 154 Ω·cm$^2$ at t$_o$ (time of peptide injection) and 153 Ω·cm$^2$ after 24 hours of incubation with peptide. Once again, the presence of the peptide did not significantly affect the functionality of tight junctions since the transendothelial resistance remained >100 Ω·cm$^2$.

The peptide concentrations recovered in the upper compartment are presented on FIG. 8.

One should note in the case of the bEnd-3/CTX barrier system a biphasic transport process with a very high rate in the first two minutes followed by a more classic kinetics.

2.4. Conclusion.

With the aim to compare the efficiency of the three BBB systems used to study the passage of the chimeric peptide, we have plotted the concentration of peptide recovered in the upper compartment after 1 hr and 24 hr of incubation. The histograms shown on FIGS. 9A and 9B indicated that the results obtained are remarkably convergent.

The experiment with PBS alone showed that the cells do not produce any contaminant that could interfere with our dosing method for the chimeric peptide (A230/A275). Overall, the bEnd-3/C6 co-culture system gave the best combined results at lhr and 24 hr.

Finally, as shown on FIG. 10, the inventors have checked that the appearance of the chimeric peptide in the upper (acceptor, triangles) compartment through the reconstituted endothelial barrier was counterbalanced by its progressive disappearance from the lower (donor, rounds) compartment.

In conclusion, these data indicated the chimeric peptide is transported from one side to the other side of a reconstituted BBB (bEnd-3 cells either pure or co-cultured with two types of glial cells).

Example 3: The Chimeric Peptide Blocks the Ca$^{2+}$ Fluxes Induced by the Formation of Oligomeric Amyloid Pores of α-Synuclein, the Protein Associated with Parkinson's Disease In Example 1 (FIG. 5), the inventors showed that the chimeric peptide cured neural cells (SH-SY5Y cells) intoxicated by Alzheimer's β-amyloid peptides. Specifically, they showed that upon incubation with Alzheimer's β-amyloid peptide 1-42 (220 nM), these cells suffered from the formation of oligomeric amyloid pores in their plasma membranes. These pores induced a massive entry of Ca$^{2+}$ ions from the extracellular medium. In presence of an equimolar concentration of chimeric peptide ("Pep Chim", 220 nM), these pore could no longer be formed because the peptide efficiently prevented Alzheimer's β-amyloid peptide 1-42 to interact with ganglioside GM1 at the neuronal cell surface. This is illustrated in FIG. 11A.

In contrast with Alzheimer's β-amyloid peptide 1-42, the Parkinson's disease-associated α-synuclein interacts with ganglioside GM3, not GM1. The chimeric peptide is a universal ganglioside-binding peptide that interacts with similar affinity with both GM1 and GM3. On this basis, the inventors anticipated that the chimeric peptide could cure neural cells from toxic amyloid pores formed by α-synuclein oligomers.

SH-SY5Y cells were first loaded with the Ca$^{2+}$-sensitive probe FLUO4-AM and then incubated with 220 nM of α-synuclein. This induced the formation Ca$^{2+}$-permeable amyloid pores that induced a massive entry of Ca$^{2+}$ inside the cells (FIG. 11B). When the chimeric peptide (220 nM) was injected in the cell culture together with α-synuclein, pore formation did not longer occur because the chimeric peptide prevented α-synuclein to interact with GM3 on the neuronal cell membrane. Thus, the chimeric peptide totally abrogated the Ca$^{2+}$ fluxes induced by α-synuclein.

In conclusion, it is now proven that the chimeric peptide displays anti-Alzheimer and anti-Parkinson properties in neural cell cultures.

Example 4: Synthesis and Testing of "Reversed" Peptides

Because the chimeric peptide of SEQ ID NO:3 interacts with a dimer of gangliosides forming a symmetric chalice-like surface of interaction, the inventors tested the ganglioside-binding capacity of a chimeric peptide in which the pair of Histidine residues was moved at the N-terminal part of the chimeric peptide. Hence the amino acid sequence of this so-called "reversed' chimeric peptide is KEHHGVLYVGTK (SEQ ID NO:11).

A monolayer of ganglioside GM1 or GM3 was spread at the air-water interface and the reversed chimeric peptide was injected in the aqueous subphase at a concentration of 10 µM. The interaction of the peptide with these gangliosides was assessed by real-time measurements of the surface pressure (□) of the monolayer, expressed in mN/m. The kinetics of interaction of the reversed chimeric peptide with monolayers of gangliosides GM1 and GM3 are shown in FIG. 12.

These data indicate that the reversed chimeric peptide recognizes both GM1 and GM3 gangliosides. This dual recognition is conferred by the pair of Histidine residues introduced in the frame of the alpha-synuclein 34-45 sequence. Compared with the prototype chimeric peptide of SEQ ID NO: 3 described in this invention, the "reversed chimeric peptide" of SEQ ID NO: 11 has a different location of the pair of Histidine residues. Since the biological activity of the chimeric peptide relies on the universal ganglioside-binding properties conferred by the pair of Histidine residues, the inventors expect the reversed chimeric peptide to show interesting anti-Alzheimer, anti-Parkinson, anti-Creutzfeldt-Jakob, anti-viral, anti-bacterial and anti-0 properties as well.

REFERENCES

Daniotti et al, Frontiers in Oncology, 2013, vol 3, article 306:1-12;

Di Scala C, Troadec J D, Lelièvre C, Garmy N, Fantini J, Chahinian H (2014). Mechanism of cholesterol-assisted oligomeric channel formation by a short Alzheimer β-amyloid peptide. J Neurochem 128: 186-195.

Fantini J (2003) How sphingolipids bind and shape proteins: molecular basis of lipid-protein interactions in lipid shells, rafts and related biomembrane domains. Cell Mol Life Sci 60: 1027-1032.

Fantini J, Yahi N (2010) Molecular insights into amyloid regulation by membrane cholesterol and sphingolipids: common mechanisms in neurodegenerative diseases. Expert Rev Mol Med 12:e27.

Fantini J, Yahi N (2011a) Molecular basis for the glycosphingolipid-binding specificity of α-synuclein: key role of tyrosine 39 in membrane insertion. J Mol Biol 408: 654-669.

Fantini J, Carlus D, Yahi N (2011b) The fusogenic tilted peptide (67-78) of α-synuclein is a cholesterol binding domain. Biochim Biophys Acta 1808: 2343-2351.

Fantini J, Yahi N, Garmy N (2013) Cholesterol accelerates the binding of Alzheimer's β-amyloid peptide to ganglioside GM1 through a universal hydrogen-bond-dependent sterol tuning of glycolipid conformation. Front Physiol 4: 120.

Fantini J, Di Scala C, Yahi N, Troadec J D, Sadelli K, Chahinian H, Garmy N (2014). Bexarotene blocks calcium-permeable ion channels formed by neurotoxic Alzheimer's β-amyloid peptides. ACS Chem Neurosci, January 2. [Epub ahead of print]

Guex, N. and Peitsch, M. C. (1997) SWISS-MODEL and the Swiss-PdbViewer: An environment for comparative protein modeling. Electrophoresis 18, 2714-2723.

Lingwood D, Binnington B, Rog T, Vattulainen I, Grzybek M, Coskun U, Lingwood C A, Simons K (2011) Cholesterol modulates glycolipid conformation and receptor activity. Nat Chem Biol 7: 260-262.

Oikawa, N., Yamaguchi, H., Ogino, K., Taki, T., Yuyama, K., Yamamoto, N., Shin, R. W., Furukawa, K. & Yanagisawa, K. (2009). Gangliosides determine the amyloid pathology of Alzheimer's disease. Neuroreport 20, 1043-1046.

Radhakrishnan A, Anderson T G, McConnell H M (2000) Condensed complexes, rafts, and the chemical activity of cholesterol in membranes. Proc Natl Acad Sci USA 97:12422-12427.

Thakur G, Micic M, Leblanc R M (2009) Surface chemistry of Alzheimer's disease: A Langmuir monolayer approach. Colloids Surf. B Biointerfaces 74: 436-456.

Thomsen R, Christensen M H (2006) MolDock: A New Technique for High-Accuracy Molecular Docking. J Med Chem 49: 3315-3321.

Yahi N, Aulas A, Fantini J (2010) How cholesterol constrains glycolipid conformation for optimal recognition of Alzheimer's beta amyloid peptide (Abeta1-40). PLoS One 5: e9079.

Wu G, Lu Z H, Kulkarni N, Ledeen R W (2012) Deficiency of ganglioside GM1 correlates with Parkinson's disease in mice and humans. J Neurosci Res 90, 1997-2008.

The invention claimed is:

1. A peptide comprising:
   a) the amino acid sequence EGVLYVGHHT (SEQ ID NO: 1), or
   b) the amino acid sequence EGVLYVGHHT (SEQ ID NO: 1) and one or more chemical modifications that protect the peptide against proteolysis;
   wherein the total length of the peptide is between 12 and 20 amino acids.

2. A peptide of claim 1, wherein at least the final N-terminal and C-terminal amino acids of the peptide are basic amino acids selected from lysine, arginine and histidine.

3. A peptide of claim 2, comprising or consisting of $X_5$-EGVLYVGHHT-$X_6$ (SEQ ID NO: 2), wherein $X_5$ and $X_6$ are independently lysine, arginine, or histidine.

4. A peptide of claim 3, which consists of KEGVLYVGHHTK (SEQ ID NO: 3).

5. A peptide of claim 3, which consists of REGVLYVGHHTR (SEQ ID NO: 6), REGVLYVGHHTK (SEQ ID NO: 7), or KEGVLYVGHHTR (SEQ ID NO: 8).

6. A nucleic acid encoding a peptide of claim 1.

7. A pharmaceutical composition comprising a peptide of claim 1 and a pharmaceutically-acceptable carrier.

8. A method for treating a condition which involves adhesion to a cell membrane ganglioside in a subject, comprising administering a peptide of claim 1 to a subject in need thereof, wherein the condition is Alzheimer's disease or Parkinson's disease.

* * * * *

UNITED STATES PATENT AND TRADEMARK OFFICE
CERTIFICATE OF CORRECTION

PATENT NO. : 10,087,226 B2
APPLICATION NO. : 15/125237
DATED : October 2, 2018
INVENTOR(S) : Jacques Fantini et al.

It is certified that error appears in the above-identified patent and that said Letters Patent is hereby corrected as shown below:

On the Title Page

Item (71) should read as follows:
--(71) Applicant: Universite D'Aix-Marseilles, Marseilles (FR)--

Signed and Sealed this
Twenty-seventh Day of August, 2019

Andrei Iancu
*Director of the United States Patent and Trademark Office*